US005595870A

United States Patent [19]
Knapp et al.

[11] Patent Number: 5,595,870
[45] Date of Patent: Jan. 21, 1997

[54] IDENTIFYING NUCLEIC ACIDS BY RESTRICTION DIGESTION AND HYBRIDIZATION WITH RANDOM OR PSEUDORANDOM OLIGONUCLEOTIDES

[75] Inventors: Michael R. Knapp; Philip Goelet, both of New York, N.Y.

[73] Assignee: The Trustees of Columbia University in the City of New York, New York, N.Y.

[21] Appl. No.: 106,143

[22] Filed: Aug. 13, 1993

Related U.S. Application Data

[63] Continuation of Ser. No. 982,416, Nov. 27, 1992, abandoned, which is a continuation of Ser. No. 857,675, Mar. 25, 1992, abandoned, which is a continuation of Ser. No. 312,596, Feb. 17, 1989, abandoned.

[51] Int. Cl.[6] .................................................. C12Q 1/68
[52] U.S. Cl. ............................................... 435/6; 436/94
[58] Field of Search ........................ 435/6, 91.2; 935/78; 436/501, 504, 94

[56] References Cited

U.S. PATENT DOCUMENTS

| | | | |
|---|---|---|---|
| 4,689,295 | 8/1987 | Taber et al. | 435/6 |
| 4,717,653 | 1/1988 | Webster, Jr. | 435/5 |
| 4,847,201 | 7/1989 | Kaswasaki et al. | 435/70 |
| 5,002,867 | 3/1991 | Macevicz | 435/6 |
| 5,087,558 | 2/1992 | Webster, Jr. | 435/5 |
| 5,126,239 | 6/1992 | Livak et al. | 435/6 |

OTHER PUBLICATIONS

Vergnaud, *Nucleic Acids Res.* 17(19), 7623–7630 (11 Oct. 1989).
Kashi et al., *Mammalian Genome*, 5, 525–530 (1994).
Koschinsky et al., *Proc. Natl. Acad. Sci. USA* 83, 5086–5090 (1986).
Pande et al., Proc. Natl. Acad. Sci., USA, 81, Aug. 1984, pp. 4965–4969.

*Primary Examiner*—Kenneth R. Horlick
*Attorney, Agent, or Firm*—John P. White

[57] ABSTRACT

This invention provides a method of determining whether a nucleic acid molecule having a sequence of interest is present within a nucleic acid-containing sample which comprises the steps: (A) subjecting said nucleic acid of said sample to a treatment sufficient to fragment said nucleic acid and to produce a plurality of fragments derived from said nucleic acid; (B) fractionating said plurality of fragments; (C) contacting said fractionated plurality of fragments, under hybridizing conditions, with a reagent comprising a mixture of random or pseudorandom oligonucleotides, said oligonucleotides having a length a $\geq 3$ and $\leq 1000$ nucleotides; (D) detecting the pattern of hybrids that form from said contacting of said fractionated nucleic acid molecules and said oligonucleotides of the mixture of random or pseudorandom oligonucleotides; and (E) determining whether said nucleic acid molecule having said sequence of interest is present in said sample by determining whether said pattern is indicative of the presence of said molecule. This invention provides a method of obtaining a signature for a nucleic acid of interest and for constructing a restriction map of a nucleic acid of interest. This invention finally provides a method of identifying a nucleic acid sequence which encodes, directly or indirectly, a particular biological activity of interest.

19 Claims, 3 Drawing Sheets

1% AGAROSE GEL

FIGURE 1

1% AGAROSE GEL

IDENTIFYING NUCLEIC ACIDS BY RESTRICTION DIGESTION AND HYBRIDIZATION WITH RANDOM OR PSEUDORANDOM OLIGONUCLEOTIDES

This is a continuation of application Ser. No. 982,416, filed Nov. 27, 1992, abandoned, which is a continuation of application Ser. No. 857,675 filed Mar. 25, 1992, abandoned, which is a continuation of application Ser. No. 312,596, filed Feb. 17, 1989, abandoned.

BACKGROUND OF THE INVENTION

Within this application several publications are referenced by Arabic numerals. Full citations for these references may be found at the end of the specification immediately preceding the claims. The disclosures of these publications in their entirety are hereby incorporated by reference into this application in order to more fully describe the state of the art to which this invention pertains.

It is often desirable to isolate unknown biomolecules, particularly biomolecules which are related to a biological process or condition of interest. Unfortunately, this is seldom accomplished without great difficulty, due to several reasons often including a lack of suitable probes and any information concerning the structure or identity of the biomolecule of interest.

It is theoretically possible to isolate a biomolecule of interest by obtaining a pool of hybrids which contains at least one member which incorporates or expresses the biomolecule of interest. One may then proceed to use various techniques to eliminate the members of the pool which are not related to the biomolecule of interest. Unfortunately, such a process would require so many elimination steps that the period of time required for its completion would be so great as to render it impractical.

The most comprehensive technique used in genetic analysis is DNA sequencing. In addition to DNA sequencing, there are other less comprehensive techniques used to identify DNA sequence variability which may be used for purposes such as genetic diagnosis and fingerprinting. These methods make use of DNA sequence recognition by enzymes or nucleic acids.

The sequence-specific cleavage of DNA by restriction endonucleases and the separation of the resulting fragments by gel electrophoresis have been used as core technologies in the physical analysis of DNA. The ability of nucleic acids to form hydrogen-bonded hybrids with complementary nucleic acid strands that are either in solution or immobilized on solid phase substrates has been exploited by techniques which utilize nucleic acid sequences as labelled hybridization probes (1–4). The combined use of these physical and chemical methods in the study of restriction fragment length polymorphisms (RFLPs) has permitted the identification of genetic variants in human populations, and is being used as a method for genetic fingerprinting and mapping (5–7).

With the advent of recombinant DNA technology, the ability of nucleic acids to form hydrogen-bonded hybrids with complementary strands in solution or immobilized on solid-phase substrates has been widely exploited as a means for the characterization and analysis of gene structure and function. The isolation of a gene or mRNA as a recombinant molecule allows for the selective amplification and purification of that sequence. It is then possible to label that nucleotide sequence by a variety of techniques in order to specifically probe populations of nucleic acids for the presence of that particular sequence.

Initially, virtually all hybridization probes were produced in bacteria via the amplification of recombinant plasmids in that host. Improvements in solid phase synthesis of DNA have presented alternative ways to generate hybridization probes, as well as many other new ways to manipulate nucleic acids in vitro (8). For example, one may generate oligonucleotide probes using information gleaned from the literature or peptide sequence data.

One of the most widely used applications of the knowledge of the genetic code is the utilization of a complementary technology, protein chemistry, to further understand a system of interest. For any given sequence of amino acids, however, the genetic code does not always indicate an unambiguous nucleotide choice. For this reason, a nucleotide probe corresponding to a given amino acid sequence is typically a mixture of oligonucleotides which may be synthesized simultaneously and which correspond to all possible nucleotide sequences capable of coding for the peptide sequence.

Using current methods for solid phase synthesis of deoxyoligonucleotides, it is possible to synthesize mixed oligonucleotide DNA sequences of similar or identical lengths by coupling nucleotide mixtures at various condensation cycles. The number of different oligonucleotides generated in such a synthesis is increased at each condensation cycle by the multiple of the number of nucleotides used in each cycle. In this way both the number and specific sequences of oligonucleotide species in a given synthesis may be programmed. Oligonucleotide mixtures may also be generated by mixing independently synthesized mixtures of oligonucleotides. Pseudorandom and random mixtures of oligonucleotides may be generated by mixing in an arbitrary fashion independently synthesized oligonucleotides (9).

This synthetic chemistry may be used to design mixtures of oligonucleotides with random and pseudorandom sequences in order to develop a battery of probes whose hybridization patterns to target DNAs may be used for genetic analysis. The reagents and methods of the subject invention are based upon the statistical features of essentially random occurrences of nucleotides in target DNAs and the representation of these occurrences as revealed by DNA hybridization.

SUMMARY OF THE INVENTION

This invention provides a reagent useful for typing a nucleic acid of interest which comprises at least one discrete pseudorandom mixture of oligonucleotides, each oligonucleotide in each such mixture having a predetermined length and a predefined sequence and the number of oligonucleotides in each such mixture being ≧2.

This invention also provides a reagent useful for typing a nucleic acid of interest which comprises at least one discrete random mixture of oligonucleotides, each oligonucleotide in each such mixture having a predetermined length and a predefined sequence and the number of oligonucleotides in each such mixture being ≧2.

This invention also provides a method of determining whether a nucleic acid sequence is present within a nucleic acid-containing sample which comprises contacting the sample, under hybridizing conditions, with the reagent of the subjection invention, wherein the reagent comprises an oligonucleotide having a nucleic acid sequence sufficiently complementary to such nucleic acid sequence to permit the formation of a detectable hybrid therewith; detecting the presence of hybrids formed between the nucleic acid of interest and such oligonucleotide; and thereby determining whether the nucleic acid sequence is present in the nucleic acid-containing sample.

This invention also provides a method of determining the concentration of a nucleic acid of interest present within a nucleic acid-containing sample which comprises contacting the sample, under hybridizing conditions, with a known amount of the reagent of the subject invention, wherein the regent comprises an oligonucleotide having a nucleic acid sequence sufficiently complementary to such nucleic acid of interest to permit the formation of a detectable hybrid therewith; determining the concentration of hybrids formed between the nucleic acid of interest and such oligonucleotide; and thereby determining the concentration of the nucleic acid of interest in the nucleic acid-containing sample.

This invention also provides a method of obtaining a signature for a nucleic acid of interest which comprises determining the presence of a plurality of nucleic acid sequences within a sample containing the nucleic acid of interest, and obtaining from such determination a signature for the nucleic acid of interest.

This invention also provides a method of constructing a restriction map of a nucleic acid of interest which comprises preparing at least two samples containing different restriction enzyme digests of the nucleic acid of interest; independently determining the presence of a plurality of nucleic acid sequences within each such sample; and obtaining from such determinations a restriction map of the nucleic acid of the nucleic acid of interest.

This invention further provides a method of identifying a nucleic acid sequence which encodes, directly or indirectly, a particular biological activity of interest which comprises contacting a plurality of nucleic acid-containing samples with the reagent under hybridizing conditions; assaying the resulting samples to determine whether the biological activity of interest has been altered and thus identifying samples in which the biological activity has been altered; determining the oligonucleotide which has or oligonucleotides which have, hybridized to the nucleic acid contained in such samples; and from such determination identifying the nucleic acid sequence which encodes such biological activity of interest.

DETAILED DESCRIPTION OF THE INVENTION

This invention provides a reagent useful for typing a nucleic acid of interest which comprises at least one discrete pseudorandom mixture of oligonucleotides, each oligonucleotide in each such mixture having a predetermined length and a predefined sequence and the number of oligonucleotides in each such mixture being $\geq 2$.

Typing may comprise qualitatively or quantitatively determining the presence of a nucleic acid of interest. Alternatively, typing may comprise analyzing the primary structure of a nucleic acid of interest.

A nucleic acid of interest may be any type of DNA, RNA or combination thereof. Examples of nucleic acids of interest include: DNA encoding a structural gene connected with a known biological function; DNA which functions as a unit that regulates the transcription of a particular gene; and mRNA molecules whose abundance is altered in a phenotypic mutation.

The probability of the complement of a specific sequence within an oligonucleotide probe existing within target DNA of known length may be calculated.

In fact, virtually all techniques relating to recombinant DNA technology take into consideration the essentially normal distribution of dA, dC, dG, and dT in DNA and A, G, C, and U in RNA (11). For example, experiments involving restriction analyses of genomic DNA and the generation of libraries of recombinant DNA rely on probabilistic calculations based on this distribution.

The probability of a particular nucleotide appearing at a given position in a nucleotide sequence is ¼ or 0.25 assuming that 4 nucleotide choices are possible. The frequency of occurrence of a particular nucleotide sequence of length n is therefore 0.25 to the nth power or $(0.25)^n$. For n=12 nucleotides, the possibility of finding a particular sequence of this length is $(0.25)^{12} = 5.96 * 10^{-8}$, an extremely small number (although certainly not negligible considering the haploid human genome is composed of nearly $10^{10}$ nucleotides).

It is possible to calculate the probability (u) of finding a sequence of length n within a longer sequence of nucleotides. To do this, the total number of sequences (which is the number of chances of finding a sequence matching a given sequence of n length) of n length within the longer sequence must be calculated. The number (y) of possible sequences of length n within a sequence of length x is given by the formula y=(x−n) +1. For example, the number of sequences of 12nucleotides in length (12-mers) to be found within a sequence of 12 nucleotides is (13−12)+1=2. Since the two sub-sequences may be thought of as independent tries at finding the given 12-mer, the probabilities are additive giving a new probability $u = (5.96 * 10^{-8}) + (5.96 * 10^{-8}) = 1.19 * 10^{-7}$. As the length of the target DNA sequence increases, the probability (u) increases. In a string 10000 nucleotides in length, the probability (u) of finding any random 12-mer becomes $(5.96 \times 10^{-8}) \times [(10000-12)+1] = 5.95 * 10^{-4}$.

The probability of finding a sequence of 12 nucleotides within a mixture of individual oligonucleotides may be calculated by multiplying the probability (u) for each individual oligonucleotide by the number of oligonucleotides. In the above illustration, the probability of finding any one of a mixture of 100 different 12-mers within a given sequence of 10000 nucleotides is calculated by multiplying the probability of finding one 12-mer by 100 (ie. $(5.95 \times 10^{-4}) \times 100 = 0.0595$).

In statistical terms, the probability u represents the average expected frequency of the event in question, the apex of the curve describing the frequency distribution. If the probability of an event is small and number of trials large, the Poissonian relation may be used to calculate the probability (p) of finding a specific number (r) of events, given the predicted frequency (u) described above, P(r) has the calculated mean probability as follows:

$$p(r) = \frac{e^{-u} \times u^r}{r!}$$

where p=probability of r events
e=base of natural logarithms (2.71828)
u=predicted average frequency of events
r=number of events Thus the probability of finding 0 occurrences of a given 12-mer in a sequence of 10000 is calculated as follows:

$$p(0) = \frac{e^{-0.000595} \times (0.000595)^0}{0!}$$

$$p(0) = 0.9995.$$

The probability of not finding any occurrences given a mixture of 100 12-mers is $e^{-0.0595}=0.942$. In this way the probability for any number (r) of events can be calculated.

Although the probability of finding a defined sequence at a given frequency within a target DNA can be calculated, the biochemical representation of its presence is determined by the stability of the hybrid duplex formed by the probing sequence and its sequence.

Several sequences within an oligonucleotide can act as potential sites for hybridization to a DNA target. The effectiveness of these potential probing sequences depends upon the lengths of sequence complimentarity between the oligonucleotide and the target DNA, and the hybridization conditions used. The probability of finding an n base-pair complementary sequence in a target DNA is 8 times lower than the probability of finding an n−1 base pair complementary sequence between the same oligonucleotide and the same target DNA. The probability of finding the n−1 base-pair complementary is four times lower because the probability of finding a given sequence of n nucleotides is $(0.25)^n$, and a further two times lower because within a sequence of n nucleotides there are 2 possible n−1 nucleotide sequences.

In addition, the degree of representation of subsequences within a given oligonucleotide mixture may differ depending upon the specific design used in their synthesis. If the target DNA is in molar excess of the probing oligonucleotides, variations in the molar representation of different probing sequences will effect their relative hybridization signals.

Since, in the DNA double helix, there exist 3 hydrogen bonds between G:C base pairs and 2 hydrogen bonds between A:T pairs, G:C base pairs are approximately 1.5 times stronger than A:T base pairs. For this reason, an oligonucleotide of n bases consisting of only Gs and/or Cs will form hybrids with its complementary DNA sequence which are 1.5 times more stable than hybrids formed between a second oligonucleotide of equal length, consisting of only As and/or Ts and its complementary sequence. Hybridization between an oligonucleotide sequence of 8 Gs and/or Cs and its complementary DNA sequence would therefore be as stable under similar conditions to hybridization between a second oligonucleotide sequence of 12 As and/or Ts and its complementary target DNA sequence. This characteristic of base pairing under normal conditions seriously biases hybridization results towards GC-rich sequences. This bias can be circumvented under appropriate hybridization conditions. For example, it has been shown that high concentrations of tetramethyl ammonium chloride (TMAC) stabilize A:T base pairs and can be used to obtain G:C/A:T hybridization parity.

As used herein, a mixture of oligonucleotides means two or more different oligonucleotides. A first oligonucleotide is different from another oligonucleotide if the sequence of the first oligonucleotide is not identical to the sequence of another oligonucleotide within the mixture when the sequence of the first is compared with the sequence of another which has been aligned with it in parallel beginning at either the 5' or the 3' end of the oligonucleotide.

As used herein, a mixture of oligonucleotides, as defined in the preceding paragraph, is pseudorandom if the frequency of occurrence (p) of any given nucleotide at the same position in each of the oligonucleotides within the mixture (defined as a/n, where a is the number of times that such nucleotide occurs at such position and n is the number of oligonucleotides which include such position) is greater than 1/N for at least one position and does not equal 1 for 2 or more positions sharing a position periodicity of 3, where N is the total number of different nucleotides which can occur at any given position. A nucleotide position $X_k$ shares a position periodicity of 3 with a second nucleotide position if the second position can be described as $X_k+3$ h or $X_k−3$ h, where k is the nucleotide position of $X_k$ and h is any integer which is greater than or equal to 1. Additionally or alternatively, the frequency of occurrence (p) may be greater than 1/N for at least one position provided p does not equal 1 for more than 1 out of any 3 consecutive positions.

In practice, N may be any integer which is greater than or equal to 4 and less than or equal to 9. For example, if dA, dG, dC, and dT are the only nucleotides which could possibly occur at any given position within an oligonucleotide, N is equal to 4. If dA, dG, dC, dT, I, A, G, C and U are the only nucleotides which could possibly occur at any given position within an oligonucleotide, N is equal to 9.

An oligonucleotide may comprise a deoxyribonucleotide (e.g. dA, dG, dC, and dT), a ribonucleotide (e.g. A, G, C and U), or both a ribonucleotide and a deoxyribonucleotide (e.g. dA+U).

Oligonucleotide mixtures may be synthesized using current solid state methods of oligonucleotide synthesis. With this technique, mixed oligonucleotides of identical lengths may be synthesized by coupling nucleotide mixtures at various condensation cycles. Both the number and the sequences of the different oligonucleotides generated in this fashion can be controlled with considerable precision. At each condensation cycle, the p value for a particular nucleotide at any given nucleotide position may be programmed to equal any value between 0 and 1.

A pseudorandom oligonucleotide mixture may be synthesized by allowing p to be greater than 1/N for at least one nucleotide position and not equal to 1 for 2 or more positions sharing a position periodicity of 3; or p may be greater than 1/N for at least one position provided p does not equal 1 for more than 1 out of any given 3 consecutive nucleotide positions. For example, if during a given condensation cycle, a reaction mixture consisted of only one nucleotide, the p value for that nucleotide at that nucleotide position would be 1.

A pseudorandom oligonucleotide mixture may also be formed by combining 2 or more pre-existing oligonucleotides having known sequences to form a mixture, wherein p is greater than 1/N for at least one nucleotide position and not equal to 1 for 2 or more positions sharing a position periodicity of 3; or p may be greater than 1/N for at least one position provided p does not equal 1 for more than 1 out of any given 3 consecutive nucleotide positions.

The reagent of the subject invention may comprise a deoxyribonucleotide. Deoxyribonucleotides may be purchased or synthesized either manually or by an automated synthesizer.

Alternatively, the reagent of the subject invention may comprise a ribonucleotide. Ribonucleotides may be purchased or synthesized either manually or by an automated synthesizer.

Furthermore, the reagent of the subject invention may comprise a mixture wherein at least one oligonucleotide comprises both a ribonucleotide and a deoxyribonucleotide. Such an oligonucleotide may comprise stretches of ribonucleotides and deoxyribonucleotides (e.g. dAdGdCUGA), alternating ribonucleotides and deoxyribonucleotides (e.g. dAGdGCdAU) or any combination thereof.

The predetermined length of each oligonucleotide of the subject invention may be greater than or equal to 3 nucleotides.

In one embodiment of the invention, the predetermined length of each oligonucleotide of the subject invention is greater than or equal to 3 nucleotides and less than or equal to 1000 nucleotides.

In a preferred embodiment of the invention, the predetermined length of each oligonucleotide of the subject invention is greater than or equal to 4 nucleotides and less than or equal to 50 nucleotides. Oligonucleotides within this range of lengths are of sufficient length to hybridize with a target nucleic acid under hybridizing conditions, and are short enough to enable a sufficient number of random hybridizations with target nucleic acid to occur under hybridizing conditions.

The number of oligonucleotides contained in each mixture of the subject invention may be less than or equal to $10^5$. In one embodiment of the invention, the number of oligonucleotides in each mixture of the subject invention is less than or equal to $10^4$. In a preferred embodiment of the invention, the number of oligonucleotides in each mixture of the subject invention is less than or equal to $10^3$.

The reagent of the subject invention may comprise less than or equal to $10^4$ discrete mixtures of oligonucleotides. In one embodiment of the invention, the reagent of the subject invention may comprise $\leq 10^3$ discrete mixtures of oligonucleotides. In another embodiment of the invention, the reagent of the subject invention comprises greater than or equal to 2 and less than or $10^3$ discrete mixtures of oligonucleotides.

The reagent of the subject invention may contain at least one oligonucleotide which is labeled with a detectable marker. Preferably, the detectable marker is a radioactive moiety such as [$^{32}$P] or [$^3$H], a chromophore or a flourophore. Labeling of the oligonucleotide(s) may be performed enzymatically using [P] labeled ATP and the enzyme T4 polynucleotide kinase or other methods known to those skilled in the art. Similarly, a chromophore or a fluorophore may be chemically linked to an oligonucleotide using methods known to those skilled in the art.

A labeled oligonucleotide may be used as a probe capable of hybridizing to and enabling one to detect a nucleic acid sequence of interest. The detection of a labeled oligonucleotide probe may be achieved using autoradiography, florescence detection, or other methods well known to those skilled in the art.

This invention provides a reagent useful for typing a nucleic acid of interest which comprises at least one discrete random mixture of oligonucleotides, the number of oligonucleotides in each such mixture being $\geq 2$.

As used herein, a mixture of oligonucleotides, as described in the subject invention, is random if the frequency of occurrence (p) of any given nucleotide at the same position in each of the oligonucleotides within the mixture (defined as a/n, where a is the number of times that such nucleotide occurs at such position and n is the number of oligonucleotides which include such position) is equal to 1/N for all positions, where N is the total number of different nucleotides which can occur at any given position.

The reagent of the subject invention may comprise a deoxyribonucleotide. Alternatively, the reagent of the subject invention may comprise a ribonucleotide. Furthermore, the reagent of the subject invention may comprise a mixture wherein at least one oligonucleotide comprises both a ribonucleotide and a deoxyribonucleotide.

The predetermined length of each oligonucleotide of the subject invention may be greater than or equal to 3 nucleotides.

In one embodiment of the invention, the predetermined length of each oligonucleotide of the subject invention is greater than or equal to 3 nucleotides and less than or equal to 1000 nucleotides.

In a preferred embodiment of the invention, the predetermined length of each oligonucleotide of the subject invention is greater than or equal to 4 nucleotides and less than or equal to 50 nucleotides.

The number of oligonucleotides contained in each mixture of the subject invention may be less than or equal to $10^5$. In one embodiment of the invention, the number of oligonucleotides in each mixture of the subject invention is less than or equal to $10^4$. In a preferred embodiment of the invention, the number of oligonucleotides in each mixture of the subject invention is less than or equal to $10^3$.

The reagent of the subject invention may comprise less than or equal to $10^4$ discrete mixtures of oligonucleotides. In one embodiment of the invention, the reagent of the subject invention comprises $\leq 10^3$ discrete mixtures of oligonucleotides. In another embodiment of the invention, the reagent of the subject invention comprises greater than or equal to 2 and less than or equal to $10^3$ discrete mixtures of oligonucleotides.

The reagent of the subject invention may contain at least one oligonucleotide which is labeled with a detectable marker. Preferably, the detectable marker is a radioactive moiety such as [32p] or [3H], a chromophore or a flourophore.

It is often of interest to determine the concentration of a nucleic acid of interest in a nucleic acid-containing sample.

The subject invention provides a method of determining whether or not a nucleic acid sequence of interest is present within a nucleic acid-containing sample which comprises contacting the sample, under hybridizing conditions, with the reagent of the subject invention, wherein the reagent comprises an oligonucleotide having a nucleic acid sequence sufficiently complementary to such nucleic acid sequence to permit the formation of a detectable hybrid therewith; detecting the presence of the hybrids formed between the nucleic acid of interest and such oligonucleotide; and thereby determining whether the nucleic acid sequence is present in the nucleic acid-containing sample.

A nucleic acid-containing sample may be a purified sample of nucleic acid obtained by methods known to those skilled in the art.

Alternatively, a nucleic acid-containing sample may be a mixture of nucleic acids and other biomolecules, a tissue sample, or any other sample containing nucleic acid. In one embodiment of the invention, the nucleic acid-containing sample comprises nucleic acid from an organism of interest which is bound to a nitrocellulose filter.

As used herein, sufficient complementarity is the number of hydrogen-bonded base pairs which must exist between two nucleic acids in order for these nucleic acids to hybridize with each other under standard hybridizing conditions. The number of consecutive complementary nucleotide pairs which are required for hybridization to occur under normal hybridizing conditions usually falls within the range of 4 to 12 nucleotide pairs.

As used herein, a detectable hybrid is a hybrid the presence of which can be detected using autoradiography, florescence or electron microscopy, bioassays, or any other method well known to one skilled in the art.

The level of hybridization between the detectable oligonucleotide probe and the nucleic acid of interest may be determined using autoradiography, fluorescence microscopy, electron microscopy, bioassays or any other suitable method available to one skilled in the art.

The subject invention also provides a method of determining the concentration of a nucleic acid of interest present within a nucleic acid-containing sample which comprises contacting the sample, under hybridizing conditions, with a known amount of the reagent of the subject invention, wherein the reagent of the subject invention comprises an oligonucleotide having a nucleic acid sequence sufficiently complementary to such nucleic acid of interest to permit the formation of a detectable hybrid therewith; determining the concentration of hybrids formed between the nucleic acid of interest and such oligonucleotide; and thereby determining the concentration of the nucleic acid of interest in the nucleic acid-containing sample.

The ability to determine the concentration of a nucleic acid of interest present within a nucleic acid-containing sample depends on a number of parameters relating both to the reagent of the subject invention and the nucleic acid of interest whose concentration is being determined. These parameters may include the ratio of concentration of the nucleic acid of interest to its complementary oligonucleotide present in the reagent of the subject invention. For example, the concentration of nucleic acid of interest must be lower than its complementary oligonucleotide of the subject invention if the concentration of the nucleic acid of interest is to be determined.

The extent of sequence complementarity present between the reagent of the subject invention and the nucleic acid of interest may affect one's ability to determine the concentration of nucleic acid of interest. Additional factors which may affect one's ability to determine the concentration of nuclei acid of interest present in a nucleic acid-containing sample include hybridization ion concentration and hybridization temperature.

The determination of the absolute concentration of nucleic acid of interest present in a nucleic acid-containing sample may be useful in quantitative assays such as the determination of bacterial concentration, wherein the knowledge of an absolute concentration (e.g. µg/ml of DNA) of nucleic acid is required.

Alternatively, the determination of the concentration of a nucleic acid of interest present in a nucleic acid-containing sample relative to that of the same nucleic acid of interest present in another nucleic acid-containing sample may be of interest. In determining such a relative concentration, the absolute concentration of a nucleic acid of interest need not be known.

An example of the use of determining the concentration of a nucleic acid of interest present in a nucleic acid-containing sample relative to that of the same nucleic acid of interest present within a different nucleic acid-containing sample is an assay to determine whether or not a blood sample of interest contains a normal population of neutrophils which comprises: isolating RNA from a blood sample of interest and a normal blood sample; denaturing both RNA samples with formaldehyde or other denaturant; running the denatured RNA from both samples on an agarose gel using gel electrophoresis; transferring the RNA from both samples from the gel to a nitrocellulose filter and affixing the RNA to the filter using heat; contacting the filter with a reagent of the subject invention which has been shown to hybridize in a unique way to the RNA of neutrophils; washing off non-hybridized reagent; performing autoradiography on the nitrocellulose filter; determining from the autoradiograph obtained thereby the concentration of neutrophil RNA in the blood sample of interest relative to the normal blood sample; and thereby determining the concentration of neutrophils in the blood sample of interest relative to that of neutrophils in the normal blood sample.

The nucleic acid of interest as used herein may refer to any type of deoxyribonucleic acid. Deoxyribonucleic acid may comprise cNDA, A-DNA, B-DNA, Z-DNA, circular or linear DNA or any other DNA of interest. Alternatively, the nucleic acid of interest, as used herein, may refer to any type of ribonucleic acid. Ribonucleic acid may comprise rRNA, mRNA, tRNA, or any other RNA of interest.

In one embodiment of the invention, the nucleic acid-containing sample comprises genomic DNA from an organism or cDNA prepared from RNA transcripts thereof. Genomic DNA and cDNA may be prepared using methods well known to those skilled in the art. In another embodiment of the invention, the nucleic acid-containing sample comprises extragenomic DNA from an organism or cDNA prepared from RNA transcripts thereof. Extragenomic DNA may comprise chloroplast DNA, mitochondrial DNA, or other DNA which is not genomic DNA.

The nucleic acid-containing sample may be derived from any species of organism, such as Escherichia coli or Xenopus laevis. The organism may be a mammal. Furthermore, the organism may be a human.

In one embodiment of the invention, the sample containing the nucleic acid of interest comprises a restriction enzyme digest of either the genomic DNA of the organism or a cDNA library prepared from the DNA transcripts thereof. In another embodiment of the invention, the sample containing nucleic acid of interest comprises a restriction enzyme digest of the nucleic acid of interest.

A restriction enzyme digest of DNA may be obtained by contacting the DNA under suitable conditions with a restriction endonuclease. A restriction endonuclease may be EcoRI, BamHI or any other restriction endonuclease readily available to one skilled in the art. The digested DNA may be size-fractionated using gel electrophoresis, cloned using a suitable vector, or treated using other methods available to one skilled in the art.

In one embodiment of the invention, the oligonucleotide having a nucleic acid sequence sufficiently complementary to that of the nucleic acid whose presence is being determined is labeled with a detectable marker.

In another embodiment of the invention, the reagent of the subject invention comprises an oligonucleotide having a nucleic acid sequence which is substantially complementary to that of the nucleic acid whose presence is being determined.

In a further embodiment of the invention, the reagent of the subject invention comprises an oligonucleotide having a nucleic acid sequence which is fully complementary to that of the nucleic acid whose presence is being determined. As used herein, full complementarity refers to complementarity of 100% existing between nucleic acid sequences.

In another embodiment of the invention, the presence of a plurality of nucleic acid sequences within the nucleic acid-containing sample is determined, and the reagent comprises a plurality of oligonucleotides having nucleic acid sequences complementary to the nucleic acid sequences whose presence is being determined. In this embodiment, the reagent of the subject invention may comprise one or more discrete mixtures of oligonucleotides.

In another embodiment of the invention, the reagent comprises at least 2 discrete mixtures of oligonucleotides. An application of this embodiment is given in the Examples.

This invention provides a method of obtaining a signature for a nucleic acid of interest which comprises determining the presence of a plurality of nucleic acid sequences within a sample containing the nucleic acid of interest according to the method of the subject invention and obtaining from such determination a signature for the nucleic acid of interest.

As used herein, a "signature" is sufficient data reflecting the sequence complementarity between one or more oligonucleotides and a nucleic acid of interest to permit the nucleic acid to be identified by correlating such data with comparable data obtained by the same method reflecting the sequence complementarity between said oligonucleotide or oligonucleotides and a reference nucleic acid.

In one embodiment of the subject invention, the determination is effected by contacting the sample with a reagent which comprises a single discrete mixture of oligonucleotides.

A signature may be obtained by contacting a sample containing a nucleic acid of interest with a single discrete mixture of oligonucleotides and quantitatively determining the extent of sequence complementarity between one or more oligonucleotides in the mixture and the nucleic acid of interest in the sample. Thus, a signature may be obtained by separating the nucleic acid of interest from other nucleic acids in a sample using gel electrophoresis, denaturing and immobilizing the nucleic acids on a nitrocellulose filter or other suitable membrane, or drying the gel and then denaturing and hybridizing the immobilized nucleic acid molecules with a single discrete mixture of radiolabeled oligonucleotides, and obtaining an autoradiogram which reveals this hybridization pattern and thus serves as a signature.

In one embodiment of the invention, a signature may be generated by performing, under suitable conditions, enzymatic amplification of a nucleic acid of interest. In this embodiment, a reagent of the subject invention may be used as a primer, wherein the reagent comprises an oligonucleotide having a nucleic acid sequence sufficiently complementary to such nucleic acid of interest to permit the formation of a hybrid therewith; and analyzing the nucleic acid sequence of interest amplified thereby. A detailed discussion of the method and uses of this embodiment is provided in the Examples.

In another embodiment of the subject invention, the nucleic acid-containing sample comprises a restriction enzyme digest of the nucleic acid of interest.

Signatures may be used as "fingerprints" (5) of samples containing nucleic acid for the following applications: forensic medicine; paternity identification or lineage analysis; allelotyping; tissue identification; biopsy analysis; and the identification of genetic disorders and infectious diseases.

The analysis of correlations that exist between these nucleic acid signatures and phenotypic characteristics (biological, biochemical and biophysical) that can be measured or identified in the related biological samples may be used to identify nucleic acid sequences having a biological relationship with these phenotypes (10).

Examples of phenotypes that may be correlated to signatures obtained using the reagent of the subject invention include: normal variants of phenotypic traits, diseases (infectious, hereditary or undetermined); the expression of cell biological, biochemical and/or biophysical properties which may be measured using bioassays; and the arrest of such properties which may be measured by bioassays.

The analysis of similarities or differences between the nucleic acid signatures of independent nucleic acid hybridization experiments carried out on material from the same biological sample may be used to identify genetic linkage between independent nucleic acid sequences or species (6,7).

The physical linkage of independently isolated DNA sequences may be predicted and therefore be useful in DNA mapping projects.

Alternatively, signatures obtained from RNA hybridizations and DNA hybridizations may be used to identify gene/mRNA relationships.

This invention provides a method of constructing a restriction map of a nucleic acid of interest which comprises preparing at least two samples containing different restriction enzyme digests of the nucleic acid of interest, independently determining the presence of a plurality of nucleic acid sequences within each such sample according to the method of the subject invention, and obtaining from such determinations a restriction map of the nucleic acid of interest.

The different restriction enzyme digests may be prepared and then size fractioned using gel electrophoresis. The restriction fragments may then be denatured and immobilized on a nitrocellulose filter and contacted with the reagent of the subject invention, under hybridizing conditions as previously described. Hybrids formed between the restriction fragments and sufficiently complementary oligonucleotides in the reagent may be detected using autoradiography, and a restriction map may then be obtained by correlating the molecular weights of restriction fragments of the nucleic acid of interest in a manner known to those skilled in the art.

This invention still further provides a method of identifying a nucleic acid sequence which encodes, directly or indirectly, a particular biological activity of interest which comprises contacting a plurality of nucleic acid-containing samples with the reagent of the subject invention under hybridizing conditions; assaying the resulting sample to determine whether the biological activity of interest has been altered and thus identifying samples in which the biological activity has been altered; determining the oligonucleotide which has, or oligonucleotides which have, hybridized to the nucleic acid contained in such samples; and from such determination identifying the nucleic acid sequence which encodes such biological activity of interest.

The biological activity of interest may be any biological, biochemical or biophysical activity or trait, the presence or absence of which can be detected experimentally by methods available to those skilled in the art.

Certain embodiments of this invention are exemplified in the Examples which follow. The Examples are set forth to aid in an understanding of the invention but are not intended to, and should not be construed to, limit in any way the invention as set forth in the claims which follow.

EXAMPLE 1

Synthesis of Pseudorandom Oligonucleotide Mixtures Using Known Oligonucleotides

One may synthesize pseudorandom oligonucleotide mixtures by mixing two or more oligonucleotides having known sequences, wherein the resulting mixture conforms to the definition of pseudorandom as stated in the subject invention. Oligonucleotides having known sequences may be synthesized or purchased from a distributor.

EXAMPLE 2

Synthesis of Pseudorandom Oligonucleotide Mixtures

Using current methods for solid phase synthesis of deoxyoligonucleotides (for example phosphoramadite chemistry on an Applied Biosystems 380B synthesiser), one may synthesize mixed oligonucleotide DNA sequences of similar or identical lengths by coupling nucleotide mixtures at various condensation cycles. The number of different oligonucleotides generated in such a synthesis is increased at each condensation cycle by the multiple of the number of nucleotide species used in each cycle. In this way, both the number and specific sequences of oligonucleotide species in a given synthesis may be programmed.

The synthesis of 64 different oligonucleotide mixtures (RRG1..RRG64) of which the first 10 are listed in Table 1 below was programmed, each mixture containing 1728 unique, pseudorandom DNA species, 12 nucleotides in length. The 64 oligonucleotide mixtures differ from each other by 64 ($4^3$) different three-nucleotide sequence permutations at their 3' termini. In condensation cycles 3 to 8, one of 6 possible mixtures of 2 nucleotides (R, Q, P, S, V and Y; see table below) was randomly selected and coupled to the resin-linked oligonucleotide chains, bringing the number of 9 nucleotide-long resin-linked oligonucleotide species per synthesis, or pool, to 64 ($2^6$). In each of the final 3 condensation cycles, one of the 4 possible mixtures of 3 nucleotides (W, X, L, and M; see table below) was randomly selected and coupled to the resin-linked oligonucleotide chains, giving a final number of 1728 ($3^{3\times64}$) species of 12-mer oligonucleotides per synthesis. These mixtures of oligonucleotide chains were then deprotected and removed from the resin for use as one of the 64 mixtures.

TABLE 1

10 Oligonucleotide Mixtures Synthesised in Psuedorandom Fashion

Code

G = G
A = A
T = T
C = C
R = G + A
Q = T + G
P = A + T
S = G + C
V = C + A
Y = C + T
W = G + A + T
X = G + T + C
L = G + A + C
M = A + T + C

Oligonucleotide Mixtures

| Residue(5'-3') | 1 | 2 | 3 | 4 | 5 | 6 | 7 | 8 | 9 | 10 | 11 | 12 |
|---|---|---|---|---|---|---|---|---|---|---|---|---|
| Coupling cycle | 11 | 10 | 9 | 8 | 7 | 6 | 5 | 4 | 3 | 2 | 1 | (resin) |

TABLE 1-continued

| | | | | | | | | | | | |
|---|---|---|---|---|---|---|---|---|---|---|---|
| Mixture 1 | L | L | L | Y | S | S | Q | Q | R | G | G | G |
| Mixture 2 | W | W | X | R | R | R | P | Q | Y | A | G | G |
| Mixture 3 | M | L | W | Q | S | P | P | R | P | T | G | G |
| Mixture 4 | L | W | M | V | R | R | Y | R | R | C | G | G |
| Mixture 5 | L | L | X | V | S | R | Y | S | Q | G | A | G |
| Mixture 6 | M | L | M | S | R | R | Y | R | V | A | A | G |
| Mixture 7 | L | X | L | S | V | S | R | Y | R | T | A | G |
| Mixture 8 | M | M | M | P | Y | P | P | Q | R | C | A | G |
| Mixture 9 | X | W | W | V | S | Q | P | Y | R | G | T | G |
| Mixture 10 | X | L | X | P | R | Y | Y | R | S | A | T | G |

EXAMPLE 3

AD2 Genomic Restriction Mapping and Signature

Figure 1:
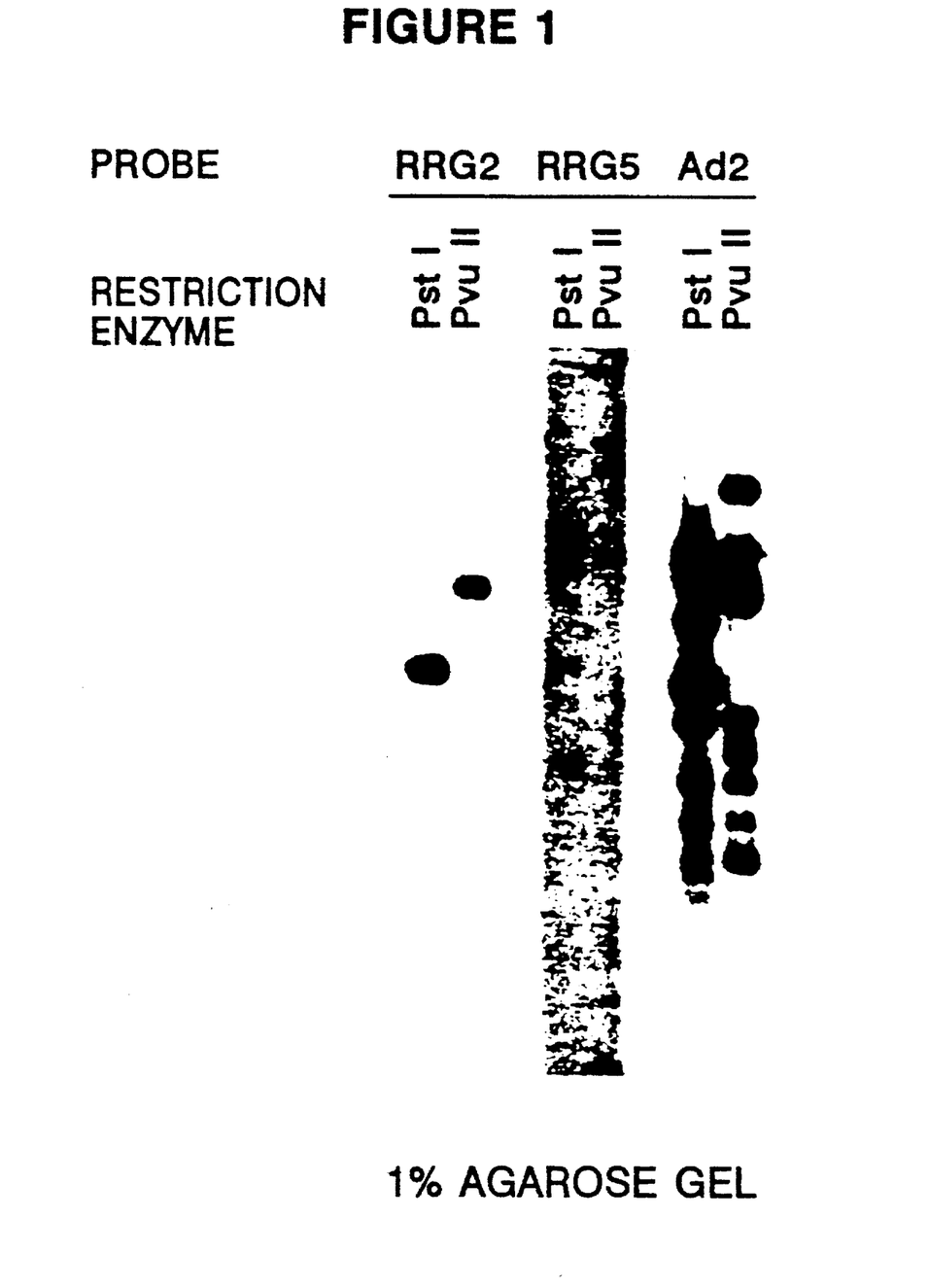
FIG. 1—Hybridization analysis of pseudorandom probes with Ad2 genomic DNA as the target DNA and RRG2 as the probe.

The target DNA, AD2 genomic DNA, was digested with two different enzymes, Pst I and Pvu II. The resulting fragments were separated on agarose gels, transferred to nylon membranes (or dried in the gel), and then hybridized to the oligonucleotide mixtures RRG2 and RRG5 which had been kinase-labelled with $^{32}$P. The results of this analysis are shown in FIG. 1.

The statistically predictable hybridization behavior of these oligonucleotide mixtures is manifested in several ways. First, the higher molecular weight restriction fragments are detected more frequently than the smaller fragments. This phenomenon is manifested by both the frequency of detection and the average level of intensity of hybridization signal obtained for the larger fragments as compared to that obtained for the smaller fragments. Both findings are consistent with the prediction that the probability of hybridization with mixtures of random or pseudorandom oligonucleotides is higher with increased target DNA length.

Second, the patterns of hybridization differ between the oligonucleotide mixtures. Although clearly visible for the larger fragments, this phenomenon is most evident for smaller fragments. In most cases with short exposure times, hybridization to the smaller fragments is not detectable. In specific cases, however, small fragments are detected and different mixtures hybridize to different small fragments. For example, in FIG. 1, it is evident that the oligonucleotide mixture RRG5 hybridizes strongly to a PstI fragment of 1463 base pairs to which oligonucleotide mixture RRG2 hybridizes minimally. In contrast, mixture RRG2 hybridizes very well to a PstI fragment of 2100 base pairs to which mixture RRG5 hybridizes relatively weakly.

Figure 2:
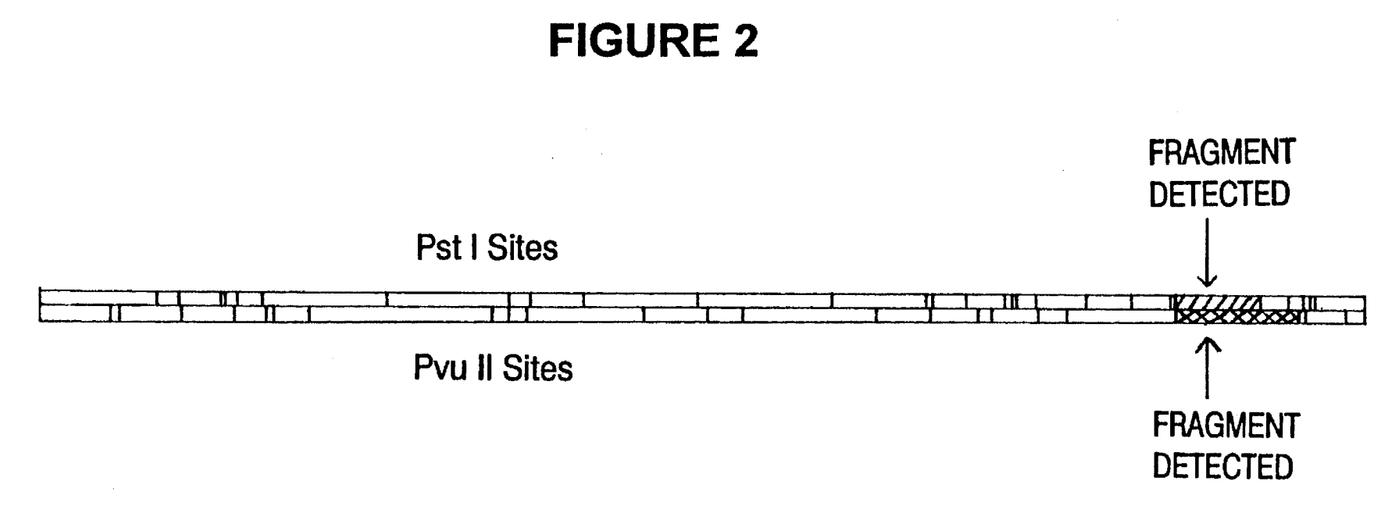
FIG. 2—Restriction map of Ad2 genomic DNA showing regions of genomic DNA which hybridize to RRG2.

Third, dramatic manifestations of the stochastic nature of the hybridization events using these oligonucleotide mixtures is occasionally seen. For example, the mixture RRG2 hybridizes particularly strongly to a PstI fragment of approximately 2100 nucleotides. Similarly there is a Pvu II fragment of approximately 3100 nucleotides in length which hybridizes extremely well. Because such strong hybridization does not happen frequently on other fragments in this genome with this mixture, it is reasonable to suspect that these two fragments contain a common stretch of Ad2 genome. Since the complete nucleotide sequence to this viral genome is known, the chromosomal positions to which these fragments correspond may be determined. As seen in FIG. 2, the two fragments which hybridize strongly to mixture RRG2 come from the same region of the genome.

The Ad2 hybridization experiment demonstrates the utility of these types of oligonucleotide reagents in the generation of nucleic acid fingerprints. The high degree of hybridization of Pst I fragment 2100 with an oligonucleotide mixture is a signature of its identity. In most cases, analyses with several mixtures will be required in order to establish a signature. Of course, the probabilistic determinations of signature generation would remain the same.

FIG. 2 shows a schematic illustration of hybridization results using oligonucleotide mixture RRG2 as a probe on Ad2 target DNA. The horizontal line depicts the linear Ad2 genome. Short vertical lines indicate restriction sites for enzymes PstI (top) and Pvu II (bottom). Heavy horizontal lines near the right of the genome indicate which fragments hybridize strongly to the RRG2 probe. The relevant PstI fragment overlaps its Pvu II counterpart over virtually its entire length.

EXAMPLE 4

The Method of DNA Amplification and Its Uses

DNA amplification may allow the detection of extremely low-abundance target sequences by sequential rounds of in vitro DNA synthesis at sites on opposite strands of a DNA molecule (12,13). The exponential accumulation of DNA rapidly results in the formation of easily detectable quantities of sequences of interest within a short experimental time.

Normally, this procedure utilizes oligonucleotide primers complementary to known sequences in a genome in order to analyze known target sequences of interest. However, the utilization of the reagent of the subject invention in this technique may provide the means for the analysis of unknown genes as well. Currently, geneticists probe for DNA sequence polymorphisms with restriction enzymes or with probes specific for a known site of mutation. Using the reagent of the subject invention as a primer for enzymatic DNA amplification, one could establish the relationship between a specific amplified DNA fragment and a phenotype of interest.

Polymorphisms of this type would be represented physically by a mutation in the primer sites, by deletions or insertions of DNA between the primer sites, or by mutations in the amplified DNA detected by other means, for example, by restriction enzyme analysis. Hybridization conditions could be established such that single base changes in the primer site would result in effective priming at that site, and therefore loss of that fragment from the amplification products.

This method has advantages over the analysis of restriction fragment length polymorphisms. In particular, the target for mutational analysis is not limited to restriction enzyme recognition sites. This may facilitate the search for DNA polymorphisms linked to phenotypes of interest. In addition, one is able to analyze many DNA sequences at once. Finally, the technique is inherently much more sensitive than genome hybridization which is normally employed to analyze RFLPs.

EXAMPLE 5

Enzymatic Amplification of Drosophila DNA

One manifestation of the ability of pseudorandom mixtures of oligonucleotides to generate signatures of DNA sequences is in the analysis of physical polymorphisms. As shown below this feature may be combined with enzymatic DNA amplification to generate, in one rapid and automatable step, large numbers of DNA fragments which manifest heritability and thus serve as genetic markers equivalent in many ways to restriction fragment length polymorphisms (RFLPs).

The technique of enzymatic DNA amplification, successive rounds of DNA synthesis form oligonucleotide primers, results in the exponential accumulation of specific DNA fragments. As discussed above, any oligonucleotide has a calculable probability of finding its complement in a target DNA. Appropriate choices for the number of oligonucleotides in a pseudorandom mixture for a given DNA to be analyzed will give a high statistical probability that the utilization of that mixture as primers of enzymatic DNA amplification will result in the amplification of specific fragments derived from the target. The success of such an experiment relies on the hybridization of members of the pseudorandom oligonucleotide mixture at a density sufficient to provide a high enough probability that the same or another member of the mixture will hybridize to the opposite strand at a close enough to the original hybridization event to be within the range (generally <10,000 bases) of the extension reaction of the first round of synthesis in the amplification procedure. Two factors determine the number of fragments which will be generated in this type of experiment: the complexity of the target DNA and the "effective" complexity of the pool.

In the example below, this technique has been employed to analyze the genomes from several species of the fruit fly Drosophila. DNA was prepared from these flies and mixed with a pseudorandom mixture made up the 2 oligonucleotides shown below. These oligonucleotides were chosen at random without regard to known or unknown Drosophila DNA sequences.

Oligo 1:5'- ATGTTGTCATGTTCTGTCTC -3'

Oligo 2:5'- CTCACGTTTAAACTCTTTGGG -3'

Figure 3:
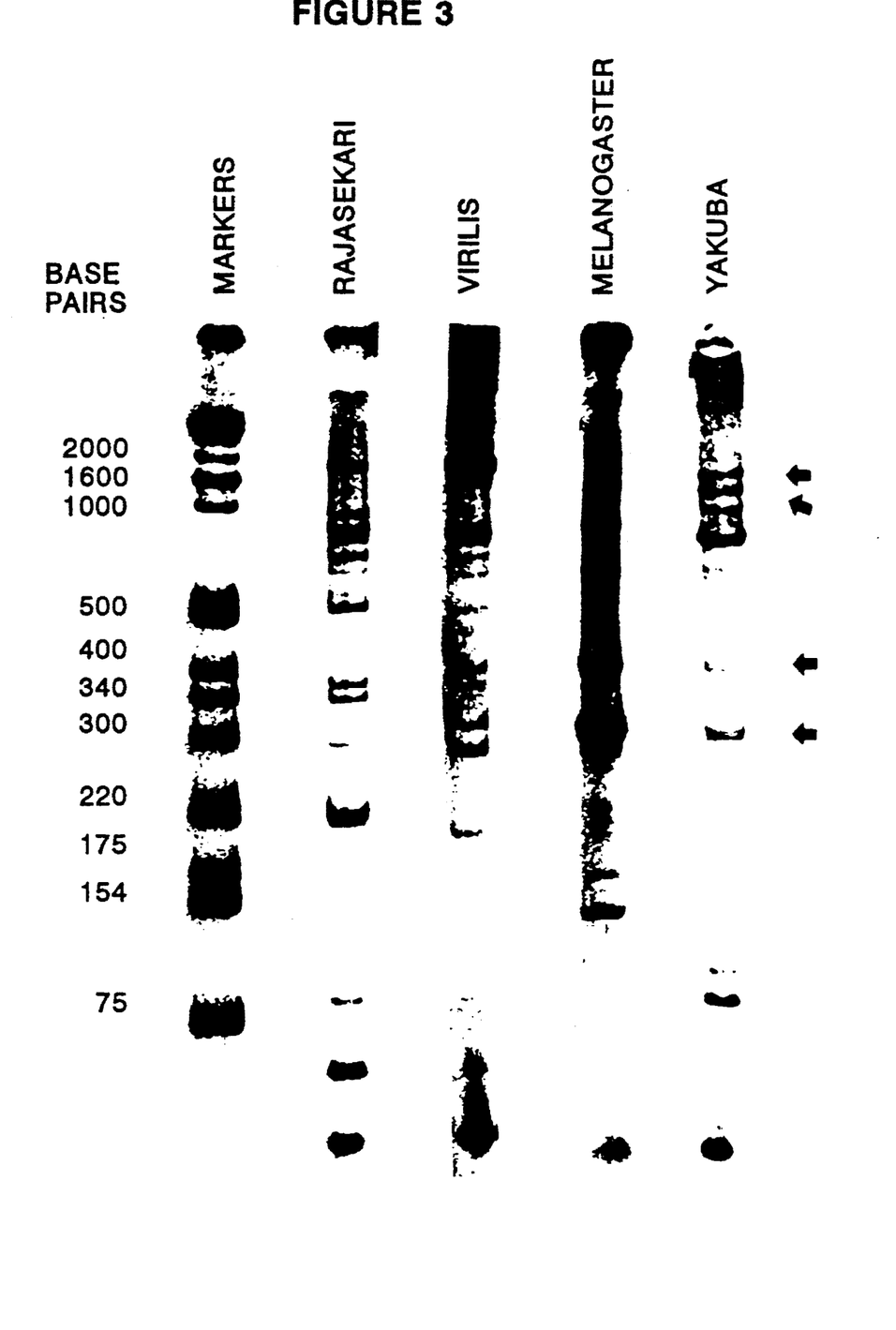
FIG. 3—Enzymatic Amplification of Drosophila genomic DNA sequences using a pseudorandom oligonucleotide mixture as a primer.

Under the appropriate conditions, the DNA and oligonucleotides were denatured and subjected to sequential rounds of denaturation, annealing and polymerase extension using the thermostable Taq polymerase. The cycles were comprised of an incubation for 2' at 95° C. to denature the double strands, an incubation for 3' at 30° C. to anneal loosely matched primers to their target sequences in the Drosophila DNA, and an incubation for 4' at 72° C. to allow the polymerase extension reaction to occur. After 20 to 30 rounds of amplification, the products were labelled with $^{32}$P and run on 5% acrylamide gels. The gels were then dried and exposed to X-ray films. The results are shown in FIG. 3.

Bands of varying intensity are apparent in the autoradiograph. This is likely due to the relative strength of interaction at 30° C. of the subsequence within the two oligonucleotides and their target in the Drosophila DNA. Differences between sequences within the site of hybridization will therefore result in changes in the representation of that band in the profile of the target DNA. Different DNA sequences may therefore be compared with respect to the generation of bands using enzymatic DNA amplification. Differences in intensity, in the extreme case being the presence or absence of a particular band, reveal differences or polymorphisms in the DNA samples being compared.

The Drosophila species *D. yakuba* diverged from *D. melanogaster* approximately 400,000 years ago while *D. rajasekari* and *D. virilis* diverged from *D. melanogaster* at least 2 million years ago. One would expect, therefore, a greater similarity between *D. yakuba* and *D. melanogaster* than between *D. melanogaster* and the other two species. This expectation is verified by the experiment shown in FIG. 3.

Comparing the lanes with the reaction products from *D. melanogaster* and *D. yakuba* DNA, one is able to discern coincident and non-coincident bands. Coincident bands are marked with arrows. Comparing the lanes with the reaction products from *D. melanogaster* with those containing the reaction products of *D. rajasekari* or *D. virilis*, one discerns only non-coincident bands. These findings are consistent with the known evolutionary relationships of these fly species and demonstrate the utility of the reagent of the subject invention for the rapid large-scale analysis of genomic DNA.

FIG. 3 shows the enzymatic amplification of Drosophila genomic DNA sequences using a pseudorandom oligonucleotide mixture as primer. Reactions were performed in 25 microliter volumes. 1 microgram of DNA was mixed on ice with 25 microliters of 10X concentrated reaction mix (500 mM KC1, 100 mM Tris pH 8.3, 15 mM mgCl$_2$, 0.1% gelatin), 2.5 microliters of 10X concentrated deoxynucleoside triphosphates (dGTP, dATP, dTTP, and dCTP at 200 micromolar), 1 microgram of pseudorandom olignonucleotide mixture primer, 2.5 units of Taq polymerase (Perkin-Elmer Cetus) and distilled water to bring the reaction volume to 25 microliters. The aqueous reaction was overlaid with 50 microliters of light mineral oil. When all reactions were assembled, the tubes were heated for 4' at 95° C. Subsequently, the tubes were subjected to 30 cycles each consisting of a denaturation step (2' at 95° C.), an annealing step (3' at 30° C.), and an extension step (4' at 72° C.). The tubes were then placed on ice. Radioactive alpha-$^{32}$P-dCTP (10 microCuries of specific activity, 1000 Curies per millimole) was added to each tube. Two more cycles were then performed as described above.

Following the last extension step, the aqueous reaction mixture was withdrawn from below the oil, brought to a volume of 100 microliters with distilled water, extracted once with an equal volume of phenol/chloroform (1:1), and precipitated with ethanol by adding 20 micrograms of glycogen, 10 microliters of 3M sodium acetate pH 4.8 and 250 microliters of 100% ethanol. After a 10 minute period of incubation on ice, the precipitate was collected by centrifugation at approximately 14,000×g at 4° C. for 10 minutes. The precipitate was washed with 100% ethanol, dried and redissolved in 20 microliters of distilled water. 10 microliters of the solution were mixed with 5 microliters of loading buffer (50% glycerol, 10 mM Tris pH 8, 1 mM EDTA, 0.1% each of bromophenol blue and xylene cyanol). This mixture was then loaded onto a 5% acrylamide gel (4.83% acrylamide, 0.1% bis-acrylamide) cast in 1X TBE (100 mM Tris base, 100 mM boric acid, 2 mM EDTA) and the gel was run at 350 volts at constant voltage with an aluminium plate clamped to the gel plates to dissipate the heat. When the bromophenol blue had migrated to ⅔ the length of the gel, electrophoresis was terminated. The gel was dried under vacuum at 80° C. and exposed to Kodak XAR X-ray film at room temperature.

References

1. Smith, C. L., Econome, J. G., Schutt, A., Kclo, S., Cantor, C. R. (1987) A Physical Map of the *Eschericia coli* K12 Genome. *Science* 236: 1448–1453.
2. Michiels, F., Craig, A. G., Zehetner, G., Smith, G. P., Lehrach, N. (1987) Molecular Approaches to Genome Analysis: A Strategy for the Construction of Ordered Overlapping Libraries. *CABIOS* 3, No. 3: 203–210.
3. Falkow, et al., U.S. Pat. No. 4,358,535, November, 1982.
4. Hames, B. D., Higgins, S. J., eds. *Nucleic acid hybridisation: a practical approach*, Oxford, Washington, D.C., 1985
5. Jeffreys, A. J., Wilson, V., Thein, S. L. (1985) Individual-specific Fingerprints of Human DNA. *Nature* 316:76–79.
6. Botstein, D., White, R. L., Skolnick, M., Davis, R. W. (1980) Construction of a genetic linkage map using restriction fragment length polymorphisms. *Am. J. of Hum. Genet.* 32:314–31.
7. Coulson, A., Sulston, J., Brenner, S., Karn, J. (1986) Towards a physical map of the genome of the nematode *C. elegans, Proc. Nat. Acad. Sci. USA* 83:7821–25.
8. Itakura, K., Rossi, J. J., Wallace, R. B. (1984) Synthesis and use of synthetic oligonucleotides. *Ann. Rev. Biochem.* 53:3223–56.
9. Goelet, P., Karn, J. (1984) Methods for cDNA cloning and sequencing tobacco mosaic virus RNA. *Gene* 29:331–42.
10. Gusella, J. F., Wesler, N. S., Conneally, P. M., Naylor, S. L., Anderson, M. A., Tanzi, R. E., Watkind, P. C., Ottina, K., Wallace, M. R., Sagauchi, A. Y., Young, A. M., Shoulson, I., Bonilla, E., Martin J. B. (1983): A polymorphic DNA marker genetically linked to Huntington's disease. *Nature* 306: 234–238.
11. Seed, B., Parker, R. C., Davidson, N. (1982) Representation of DNA sequences in recombinant DNA libraries prepared by restriction enzyme partial digestion. *Gene* 19:201–209.11.Mullis, U.S. Pat. No. 4,683, 202, July, 1987.
12. Mullis, U.S. Pat. No. 4,683,202, July 1987.
13. Saiki, A. K. Gelfand, D. H. Stoffel, S., Scharf, S. J., Higuchi, R., Horn, B. T., Mullis K. B., Erlich, H. A. (1988) Primer-directed enzymatic amplification of DNA with a thermostable DNA polymerase. *Science* 239:4839–91.

What is claimed is:

1. A method of determining whether a nucleic acid molecule having a sequence of interest is present within a nucleic acid-containing sample without having to sequence the nucleic acid in the sample which method comprises the steps:
    (A) subjecting said nucleic acid of said sample to a treatment sufficient to fragment said nucleic acid and to produce a plurality of fragments from said nucleic acid;
    (B) fractionating said plurality of fragments;
    (C) contacting said fractionated plurality of fragments, under hybridizing conditions, with a reagent comprising a mixture of random or pseudorandom oligonucleotides, said oligonucleotides having a length $\geq 3$ and $\leq 1000$ nucleotides;
    (D) detecting the pattern of hybrids that form from said contacting of said fractionated nucleic acid molecules and said oligonucleotides of the mixture of random or pseudorandom oligonucleotides;
    (E) determining whether said nucleic acid molecule having said sequence of interest is present in said sample by determining whether said pattern is indicative of the presence of said molecule.

2. The method of claim 1, wherein said mixture of oligonucleotides is a mixture of random oligonucleotides.

3. The method of claim 1, wherein said mixture of oligonucleotides is a mixture of pseudorandom oligonucleotides.

4. The method of claim 1, wherein said mixture of random or pseudorandom oligonucleotides are oligodeoxyribonucleotides.

5. The method of claim 1, wherein said mixture of random or pseudorandom oligonucleotides are oligoribonucleotides.

6. The method of claim 1, wherein said mixture of random or pseudorandom oligonucleotides is detectably labeled with a detectable marker.

7. The method of claim 1, wherein said nucleic acid of said sample comprises genomic DNA, extragenomic DNA or cDNA.

8. The method of claim 1, wherein said treatment in step (A) comprises treating said nucleic acid of said sample with a restriction endonuclease under conditions sufficient to form cleavage products.

9. A method of determining whether a nucleic acid molecule having a sequence of interest is present within a nucleic acid-containing sample without having to sequence the nucleic acid in the sample which method comprises the steps:
- (A) contacting said nucleic acid of said sample, under hybridizing conditions, with a reagent comprising a mixture of random or pseudorandom oligonucleotides, said oligonucleotides having a length $\geq 3$ and $\leq 1000$ nucleotides;
- (B) subjecting any hybridized molecules that form through said contacting to a treatment sufficient to fragment said nucleic acid and to produce a plurality of fragments derived from said nucleic acid;
- (C) fractionating said plurality of fragments;
- (D) detecting the pattern of hybrids that form from said contacting of said fractionated nucleic acid molecules and said oligonucleotides of said reagent; and
- (E) determining whether said nucleic acid molecule having said sequence of interest is present in said sample by determining whether said pattern is indicative of the presence of said molecule.

10. The method of claim 9, wherein said mixture of oligonucleotides is a mixture of random oligonucleotides.

11. The method of claim 9, wherein said mixture of oligonucleotides is a mixture of pseudorandom oligonucleotides.

12. The method of claim 9, wherein said mixture of random or pseudorandom oligonucleotides are oligodeoxyribonucleotides.

13. The method of claim 9, wherein said mixture of random or pseudorandom oligonucleotides are oligoribonucleotides.

14. The method of claim 9, wherein said mixture of random or pseudorandom oligonucleotides is detectably labelled with a detectable marker.

15. The method of claim 9, wherein said nucleic acid of said sample comprises genomic DNA, extragenomic DNA or cDNA.

16. The method of claim 9, wherein said treatment in step (A) comprises treating said nucleic acid of said sample with a restriction endonuclease under conditions sufficient to form cleavage products.

17. A method of constructing a restriction map of a nucleic acid molecule having a sequence of interest without having to sequence the nucleic acid which method comprises the steps:
- (A) treating said nucleic acid molecule with a restriction endonuclease under conditions sufficient to form cleavage products;
- (B) fractionating said cleavage fragments;
- (C) contacting said fractionated fragments, under hybridizing conditions, with a reagent comprising a mixture of random or pseudorandom oligonucleotides, said oligonucleotides having a length a $\geq 3$ and $\leq 1000$ nucleotides;
- (D) detecting the pattern of hybrids that form from said contacting of said fractionated nucleic acid molecules and said oligonucleotides of the mixture of random or pseudorandom oligonucleotides; and
- (E) determining the sites and orientation of any cleavage sites cleaved by said restriction endonuclease by evaluating said pattern.

18. The method of claim 17, wherein said mixture of oligonucleotides is a mixture of random oligonucleotides.

19. The method of claim 17, wherein said mixture of oligonucleotides is a mixture of pseudorandom oligonucleotides.

* * * * *